United States Patent [19]

Prout

[11] 4,295,466
[45] Oct. 20, 1981

[54] LIMB ENGAGING BAND FOR ORTHOTIC DEVICE

[75] Inventor: Wesley C. Prout, Los Gastos, Calif.

[73] Assignee: Hosmer/Dorrance Corporation, Campbell, Calif.

[21] Appl. No.: 150,646

[22] Filed: May 16, 1980

[51] Int. Cl.³ .............................................. A61F 3/00
[52] U.S. Cl. ................................................. 128/80 R
[58] Field of Search ...................... 128/80, 80 B, 80 D, 128/80 E, 80 G, 80 H, 80 J, 83, 83.5, 87 R, 89, 90; 2/22

[56] References Cited

U.S. PATENT DOCUMENTS

| | | | |
|---|---|---|---|
| 1,598,504 | 8/1926 | Pierce et al. | 128/80 H |
| 3,958,567 | 5/1976 | Callender, Jr. | 128/80 R |
| 4,050,455 | 9/1977 | Smith | 128/80 F |
| 4,136,404 | 1/1979 | Lange | 128/80 R X |

Primary Examiner—Stephen C. Pellegrino
Attorney, Agent, or Firm—Harris Zimmerman; Howard Cohen

[57] ABSTRACT

A limb encircling band for an orthotic device includes a generally stiff, form-retaining first member which is provided with an arcuate configuration to encircle a portion of a limb, and that includes a buckle member secured to one end thereof. A flexible, resilient second member is secured in longitudinally offset fashion from one end of the first member so that the second member extends beyond the other end of the first member. A hook and pile fastening belt is secured to the free end of the second member, and is adapted to engage the buckle joined to the first end of the first member. The first member may be bent to conform to the shape of the portion of the limb which it encompasses, and the free end of the second member may be cut to any desired length so that the band assembly may fully encompass the limb.

8 Claims, 4 Drawing Figures

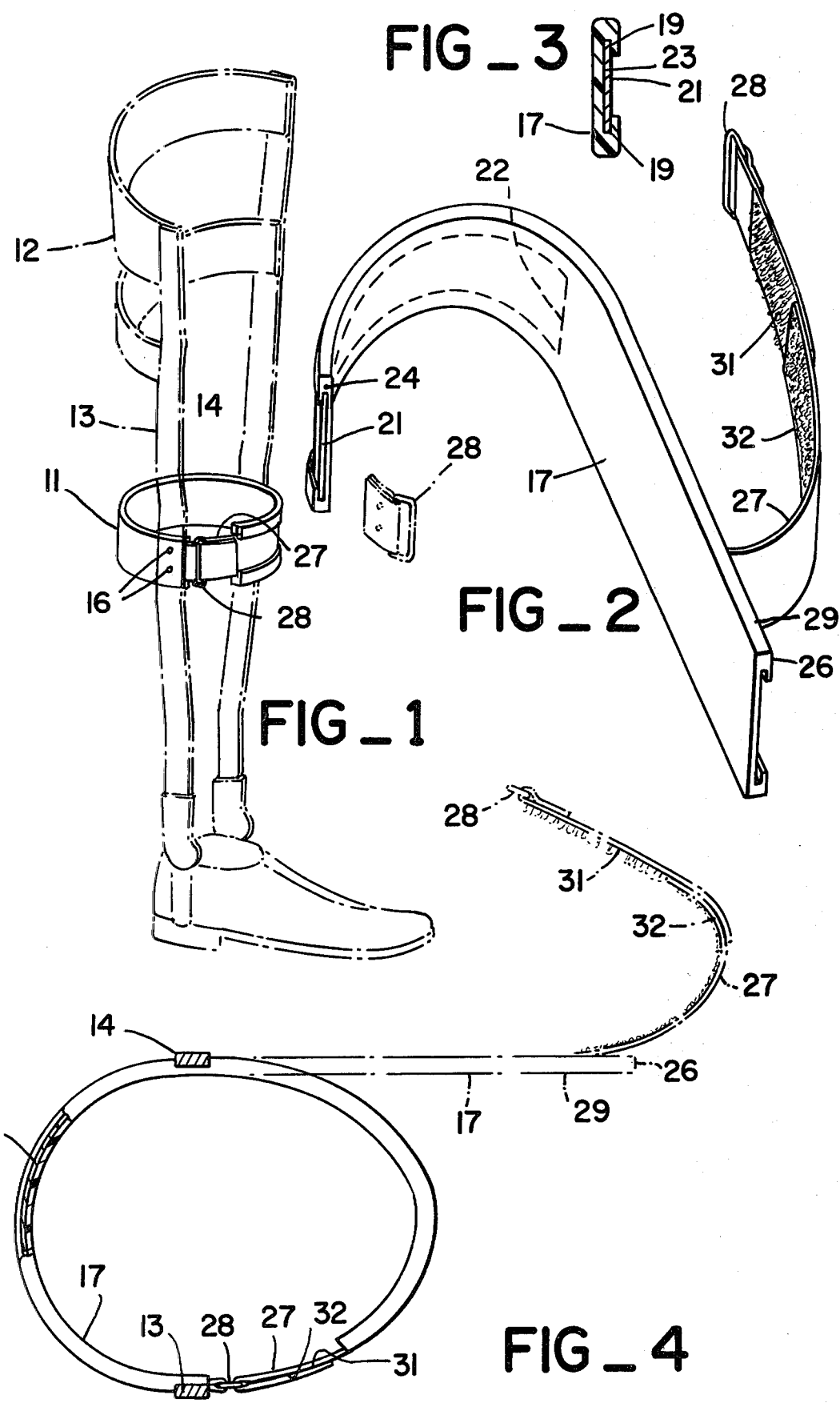

LIMB ENGAGING BAND FOR ORTHOTIC DEVICE

BACKGROUND OF THE INVENTION

An orthotic device often consists of a pair of rigid supporting members which are disposed on opposite sides of a limb. These supporting members are generally secured to the limb by means of belts or straps which are secured to the supporting members and wrap about the limb as tightly as necessary to secure the limb to the structural members.

In the prior art, the belts which secure the orthotic device to the limb have often comprised leather straps which are provided with a well-known buckle and pin fastener. These leather straps have been fitted to the limb of the wearer of the orthotic device by punching an appropriate series of holes in the tongue of the strap so that the strap may be loosened or tightened as desired by the wearer. Unfortunately, leather readily absorbs moisture, and in doing so the flexibility and length of the leather strap may change markedly. Thus after the orthotic device has been worn for a time, it has often been necessary to tighten the straps and compensate for the increased length caused by absorption of perseperation. The necessity for tightening the straps with the orthotic brace may be a source of inconvenience or embarrassement to the wearer of the brace.

In more recent times, hook and pile fastening means have been employed in conjunction with a strap and buckle to secure the orthotic brace to a limb in an infinitely adjustable manner. Although such a fastening system has many advantages over leather straps, it suffers a disadvantage in that the hook and pile web material itself lacks the rigidity to provide sufficient support to the limb. Rigidifying members have been employed in conjunction with the hook and pile fastening web, in order to overcome this deficiency. However, the rigidifying members are not easily fitted to limbs of differing widths and thicknesses. As a result, generally rigid belt assemblies employing hook and pile fasteners have been provided in a range of sizes to suit individuals of differing physiques. Manufacturing and maintaining inventories of these various belt assemblies is an added cost in the production of orthotic devices.

SUMMARY OF THE PRESENT INVENTION

The present invention generally comprises a limb encircling strap assembly which secures an orthotic device to a limb. A salient feature of the present invention is that it is adaptable to limbs of differing contours and diameters, so that the need to produce and stock strap assemblies of different lengths and widths is obviated.

The strap assembly includes an inner web contacting member which comprises a long narrow web formed of resilient, flexible material. The inner surface of the inner member is smooth, while the outer surface is provided with a longitudinally extending channel. Secured in a portion of the channel is a rigidifying member, comprising a long narrow web of stiff deformable material. One end of the rigidifying member extends beyond the respective end of the inner member, and is provided with a buckle secured to the distal end thereof.

The rigidifying member is disposed in an arcuate configuration to partially encircle a portion of the limb. The rigidifying member extends only to the approximate middle of the inner member, so that the medial portion and other end portion of the inner member is substantially resilient and flexible. Joined to the other end portion of the inner member is a hook and pile fastening strap which is adapted to engage the buckle that is cut off the end of the strap and secured to the confronting end of the rigidifying member. The hook and pile strap extends from a medial end portion of the inner member, so that the distal end portion of the inner member forms a tongue which may be employed to encircle limbs of large diameter. For limbs of smaller diameter, the tongue may be trimmed to fit the configuration of the limb, so that the buckle may be brought into confronting and abutting relationship with the remainder of the tongue when the hook and pile strap is secured tightly to the buckle. In this manner the assembly may be fitted to limbs having varying diameters, musculature, and configurations. It should be noted that the rigidifying member is secured to the longitudinally extending brace members of an orthotic device, so that the strap assembly of the present invention may secure the orthotic device to the limb.

DESCRIPTION OF THE DRAWING

FIG. 1 is a perspective view of an orthotic device which employs the strap assembly of the present invention.

FIG. 2 is a perspective view of the strap assembly of the present invention.

FIG. 3 is a cross-sectional view of a portion of a strap assembly of the present invention.

FIG. 4 is a plan view of the strap assembly of the present invention, shown in a fastened disposition.

DESCRIPTION OF THE PREFERRED EMBODIMENT

With reference to the accompanying figures, the present invention comprises a strap assembly 11 which is intended for use with an orthotic device, such as the orthotic leg brace 12 shown in FIG. 1. The strap assembly 11 is secured to the longitudinally extending bracing members 13 and 14 of the device 12, with rivets 16 or similar fasteners extending from each member 13 and 14 to the strap assembly 11. The strap assembly 11 is adapted to encircle the limb disposed within the orthotic device 12, securing the device firmly to the limb.

The strap assembly 11 includes an inner member 17 which generally comprises a long narrow panel of resilient flexible material such as foam plastic or the like. The interior surface of the member 17 which engages the surface of the limb is smooth, and the edges of the member 17 are rounded to prevent chafing or binding. The exterior surface of the member 17 is provided with a longitudinally extending groove 18, and a pair of opposed slots 19 extend laterally from the groove 18, as shown in FIG. 3.

The strap assembly also includes a rigidifying member 21 which comprises a long, narrow strip of rigid, deformable material such as steel or aluminum. The member 21 is offset longitudinally from the member 17, so that an end portion 23 extends beyond the end 24 of the member 17. Furthermore, the member 21 is substantially shorter in longitudinal extent than the member 17, so that the other end 22 of the member 21 extends only to a medial portion of the member 17, as shown in FIG. 2.

The member 21 provides a rigidity to the portion of the strap assembly which encircles the calf portion of the leg. In this manner it aids and overcomes the deficiencies of non-rigid prior art orthotic strap assemblies. Furthermore, the rigidifying member 21 is deformable so that this rigid portion of the strap assembly may be bent to conform to the configuration of the calf portion of the leg of the wearer of the orthotic brace 12. It should also be noted that the rivets 16 extend from the members 13 and 14 to the rigidifying member 21. This means of assembly to the orthotic device provides great structural strength, and assures that the orthotic device will be joined securely to the leg of the wearer.

Joined to a distal end portion of the inner member 17 adjacent to the distal end 26 thereof is a hook and pile fastening strap 27. The strap 27 has one end secured in the slots 19 of the member 17, while the other end is provided with separate hook and pile portions which are self-adhering when impinging upon each other. Such fastening straps are known in the prior art. The distal end of the strap 27 is provided with a buckle 28. The buckle 28 is cut from the strap 27 and secured to member 13 by rivets 16 during the fitting process, and is engaged by the strap 27. This engagement is accomplished by bending the freely extending portion of the member 17, as shown in phantom in FIG. 4, into a closed loop so that the end 26 confronts and generally abuts the buckle 28.

The portion of the inner member 17 between the distal end 26 thereof and the point where the fastening strap 27 joins the member 17 is generally described as tongue 29. It may be appreciated that limbs having smaller diameters do not require the entire extent of the member 17 in order to be completely encompassed and snugly engaged by the strap assembly. Recognizing this fact, the tongue portion 29 and overall length of the inner member is intended to be selectively trimmed in length during the fitting process for the orthotic device, so that the remaining length of the member 17 may almost encircle the limb of the wearer. In this configuration, the fastening strap 27 may then be employed to engage the buckle 28 to draw the distal end of the tongue 29 into confronting and abutting relationship with the buckle 23. The force provided by the fastening strap 27 causes the strap assembly to snugly engage the limb so that the orthotic device is secured to the limb. That is, the strap 27 is passed through the buckle 28 and pulled with sufficient tension to draw the strap assembly snugly about the limb. The hook portion 31 of the strap is then brought into an engagement with the confronting pile portion 32 of the strap. The self-adhesion of the hook and pile portions retain the strap assembly in the desired snug configuration.

It may be appreciated that the tongue portion 29 may be trimmed to fit a wide range of limb sizes, shapes, musculatures and the like. Furthermore, the fastening strap 27 is infinitely adjustable to provide the fit and comfort desired by the wearer. In conjunction with the rigidifying member 21, which is deformable to the contour of the rear portion of the limb, the strap assembly of the present invention provides a means for securing the orthotic device to the limb which is more easily adjustable, and suitable for a wide range of sizes and shapes, and more comfortable than strap assemblies for orthotic devices known in the prior art.

I claim:

1. A strap assembly for an orthotic device, comprising a form retaining first member including an arcuate configuration to encircle a portion of a limb; a second, flexible, resilient member having a longitudinally extending channel portion, said channel portion engaging and securing said first member; said first and second members being longitudinally offset to define a free end of each, and strap and buckle means secured to said free ends to join said free ends together in confronting relationship.

2. The strap assembly of claim 1, wherein said first and second members comprise generally flat, longitudinally extending members.

3. The strap assembly of claim 1, wherein said strap and buckle means includes a buckle secured to said free end of said first member.

4. The strap assembly of claim 3, wherein said strap and buckle means includes a strap secured in said channel of said second member and having a distal end adapted to be passed through said buckle.

5. The strap assembly of claim 4, wherein said free end of said second member includes a tongue portion adapted to be trimmed to sufficient minimum length to encircle the limb and be disposed in confronting relationship with said buckle.

6. The strap assembly of claim 4, wherein said strap includes hook and pile portions and a buckle ring which are mutually engaging.

7. The strap assembly of claim 1, wherein said first member is formed of a form retaining material which is deformable to the contours of said portion of said limb.

8. The strap assembly of claim 1, further including means for securing said first member to at least one structural member of an orthotic device.

* * * * *